US010629225B2

(12) United States Patent
Maekawa

(10) Patent No.: US 10,629,225 B2
(45) Date of Patent: Apr. 21, 2020

(54) INFORMATION PROCESSING METHOD, INFORMATION PROCESSING DEVICE, AND RECORDING MEDIUM RECORDING INFORMATION PROCESSING PROGRAM

(71) Applicant: Panasonic Intellectual Property Management Co., Ltd., Osaka (JP)

(72) Inventor: Hidetsugu Maekawa, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 103 days.

(21) Appl. No.: 16/137,247

(22) Filed: Sep. 20, 2018

(65) Prior Publication Data

US 2019/0103128 A1   Apr. 4, 2019

(30) Foreign Application Priority Data

Sep. 29, 2017   (JP) .................................. 2017-189274

(51) Int. Cl.
| G06F 17/00 | (2019.01) |
| G10L 25/63 | (2013.01) |
| G10L 15/22 | (2006.01) |
| G10L 15/04 | (2013.01) |
| G06F 16/2457 | (2019.01) |

(Continued)

(52) U.S. Cl.
CPC .......... *G10L 25/63* (2013.01); *A61B 5/02055* (2013.01); *A61B 5/165* (2013.01); *A61B 5/4803* (2013.01); *G06F 16/24575* (2019.01); *G06F 16/90332* (2019.01); *G10L 15/04* (2013.01); *G10L 15/22* (2013.01); *A61B 5/0022* (2013.01); *A61B 5/021* (2013.01); *A61B 5/024* (2013.01);

(Continued)

(58) Field of Classification Search
CPC ................................ G06F 17/00; G06F 19/00
See application file for complete search history.

(56) References Cited

U.S. PATENT DOCUMENTS

2014/0114899 A1* 4/2014 Wan .......................... G06N 5/04
706/47
2014/0188276 A1* 7/2014 Roseway .............. A61M 21/00
700/258

(Continued)

FOREIGN PATENT DOCUMENTS

JP        2010-109826        5/2010

*Primary Examiner* — Shreyans A Patel
(74) *Attorney, Agent, or Firm* — Greenblum & Bernstein, P.L.C.

(57) ABSTRACT

A first information communication device is provided with: a biological information acquisition unit that acquires biological information of a first user holding the first information processing device; a mood determination unit that detects a state in which the mood of the first user is estimated as being good on the basis of the biological information; a reason estimation unit that, in a case where a state in which the mood of the first user is estimated as being good is detected, estimates a reason for the mood of the first user being good on the basis of behavior history information indicating a behavior history of the first user; and a transmission control unit that causes a communication unit to transmit reason information indicating the estimated reason, to a second information processing device held by a second user who wishes to be notified of a timing for contacting the first user.

9 Claims, 8 Drawing Sheets

(51) Int. Cl.
  *G06F 16/9032* (2019.01)
  *A61B 5/0205* (2006.01)
  *A61B 5/00* (2006.01)
  *A61B 5/16* (2006.01)
  *A61B 5/021* (2006.01)
  *A61B 5/08* (2006.01)
  *A61B 5/024* (2006.01)
  *A61B 5/026* (2006.01)
  *A61B 5/0476* (2006.01)

(52) U.S. Cl.
  CPC .............. *A61B 5/026* (2013.01); *A61B 5/0476* (2013.01); *A61B 5/08* (2013.01); *A61B 5/7264* (2013.01)

(56) References Cited

U.S. PATENT DOCUMENTS

| | | | | |
|---|---|---|---|---|
| 2014/0191872 | A1* | 7/2014 | Gomi | G06Q 30/0201 340/573.1 |
| 2014/0214848 | A1* | 7/2014 | Devkar | G06F 16/285 707/740 |
| 2017/0297201 | A1* | 10/2017 | Shionozaki | G05D 1/0094 |
| 2018/0181854 | A1* | 6/2018 | Koukoumidis | G06N 3/006 |
| 2018/0184959 | A1* | 7/2018 | Takahashi | H04M 1/72552 |

* cited by examiner

FIG. 1
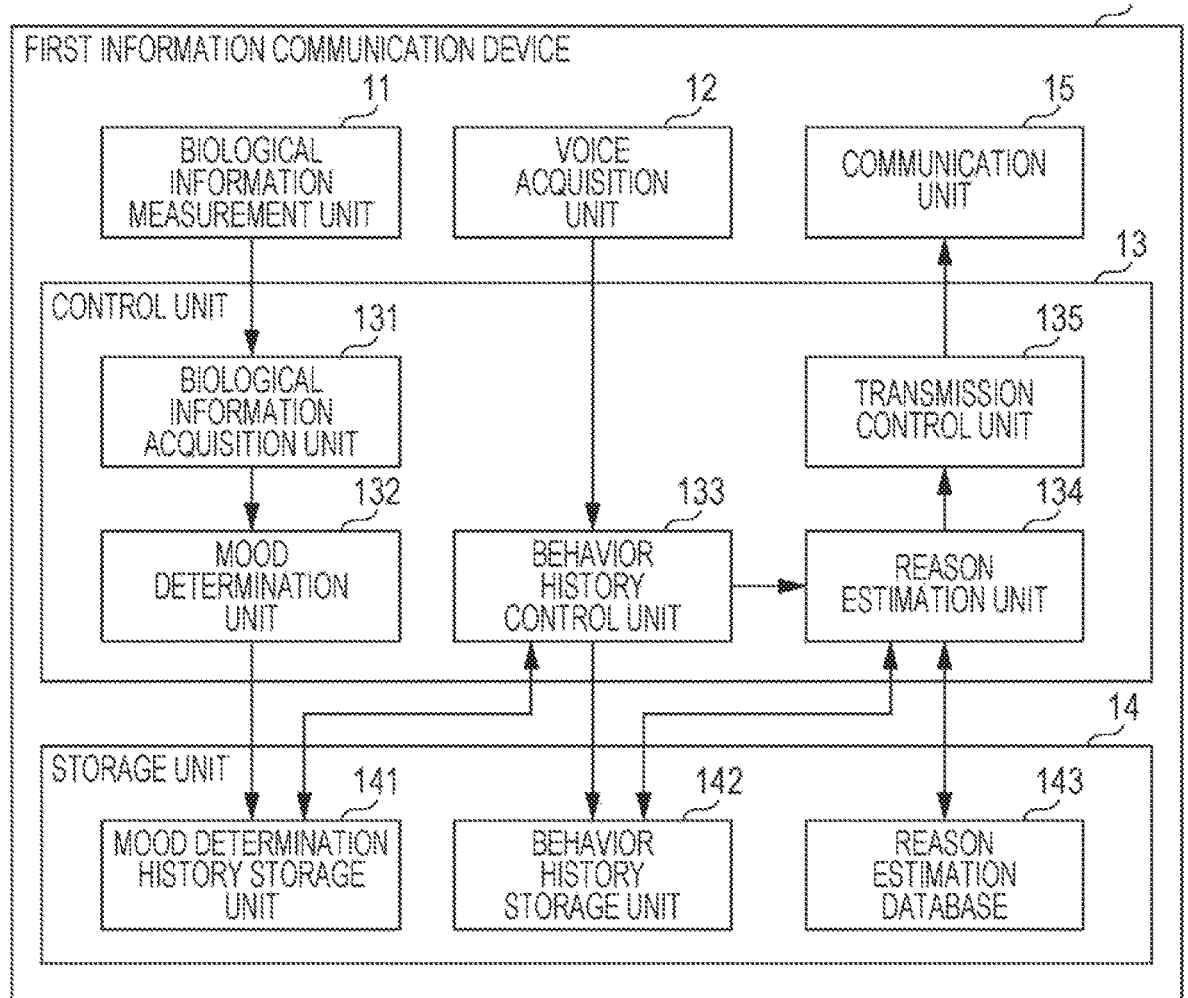
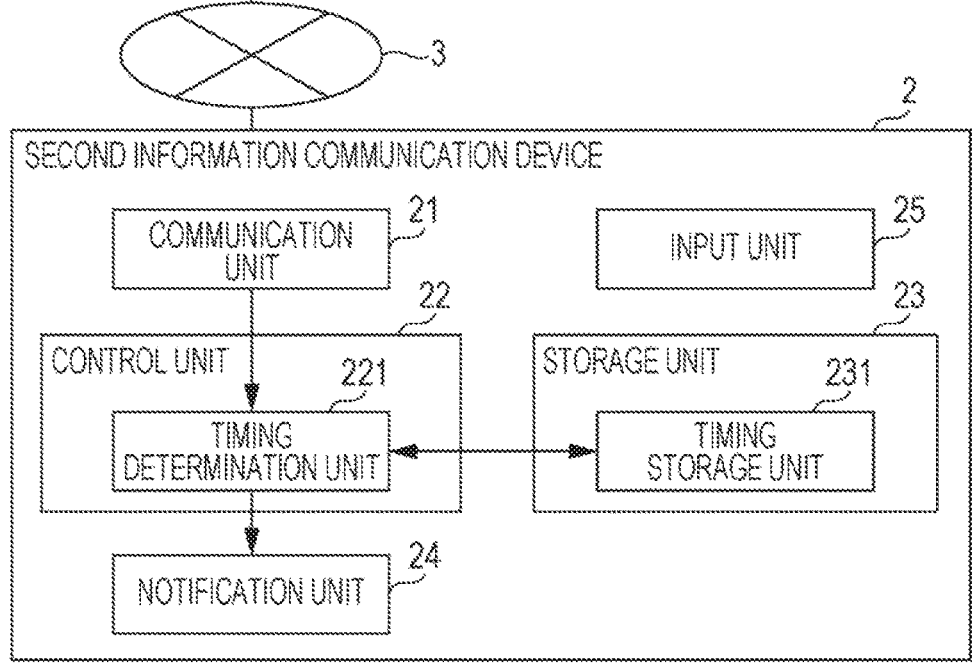

FIG. 3

| USER ID ||
|---|---|
| TIME | DEGREE OF PLEASURE |
| 10:00:00 | 2.5 |
| 10:00:15 | 3.0 |
| 10:00:30 | 3.5 |
| ... | ... |

FIG. 5

| TIME | SPEAKER | DEGREE OF PLEASURE | SPOKEN CHARACTER STRING | SPEECH ATTRIBUTE |
|---|---|---|---|---|
| 12:50:00 | FIRST USER | 3.0 | YOU DID WELL | COMPLIMENT |
| 12:50:13 | FIRST USER | 3.2 | KEEP UP THE GOOD WORK | ENCOURAGEMENT |
| ... | ... | ... | ... | ... |

FIG. 6

| SPEECH ATTRIBUTE | REASON |
|---|---|
| COMPLIMENT | PRAISE, PRAISE HIGHLY, ... |
| ENCOURAGEMENT | ENCOURAGE, PRAISE, ... |
| ... | ... |

FIG. 7

| REASON | CONTACT ADVISABILITY |
|---|---|
| PRAISE | NOT POSSIBLE |
| ENCOURAGE | POSSIBLE |
| REPRIMAND | POSSIBLE |
| ... | ... |

INFORMATION PROCESSING METHOD, INFORMATION PROCESSING DEVICE, AND RECORDING MEDIUM RECORDING INFORMATION PROCESSING PROGRAM

BACKGROUND

1. Technical Field

The present disclosure relates to an information processing method, an information processing device, and a recording medium recording an information processing program, which transmit information to another information processing device.

2. Description of the Related Art

There are prior technologies that analyze the emotions of a user and provide a service that is appropriate for the current emotion of the user.

For example, Japanese Unexamined Patent Application Publication No. 2010-109826 discloses a communication terminal device that acquires situation information with which it is possible to estimate the situation of a user including the physical situation of the user, estimates the situation of the user on the basis of the acquired situation information, and transmits information indicating the estimated situation of the user to a device of a communication partner.

Thus, in the prior communication terminal device, information with which it is possible to sufficiently comprehend the situation of the user of a transmitting-side communication terminal device can be transmitted to the user of a receiving-side communication terminal device.

SUMMARY

In one general aspect, the techniques disclosed here feature an information processing method that includes, using a processor: acquiring biological information of a first user holding a first information processing device; determining whether or not the mood of the first user is good on the basis of the biological information; in a case where it is determined that the mood of the first user is good, estimating a reason for the mood of the first user being good on the basis of behavior history information indicating a behavior history of the first user; and transmitting reason information indicating the estimated reason, to a second information processing device which is held by a second user who wishes to be notified of a timing for contacting the first user and which determines and notifies the timing on the basis of the reason information.

According to the present disclosure, a timing at which it is possible for the first user to be favorably contacted can be notified to the second user.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 1 is a block diagram depicting an example of a configuration of an information communication system according to an embodiment of the present disclosure;

FIG. 3 is a drawing depicting an example of a mood determination history stored in a mood determination history storage unit in the embodiment;

FIG. 5 is a drawing depicting an example of behavior history information accumulated by a behavior history accumulation control unit in the embodiment;

FIG. 6 is a drawing depicting an example of reason information stored in a reason estimation database in the embodiment;

FIG. 7 is a drawing depicting an example of contact advisability information stored in a timing storage unit in the embodiment;

Figure 2:
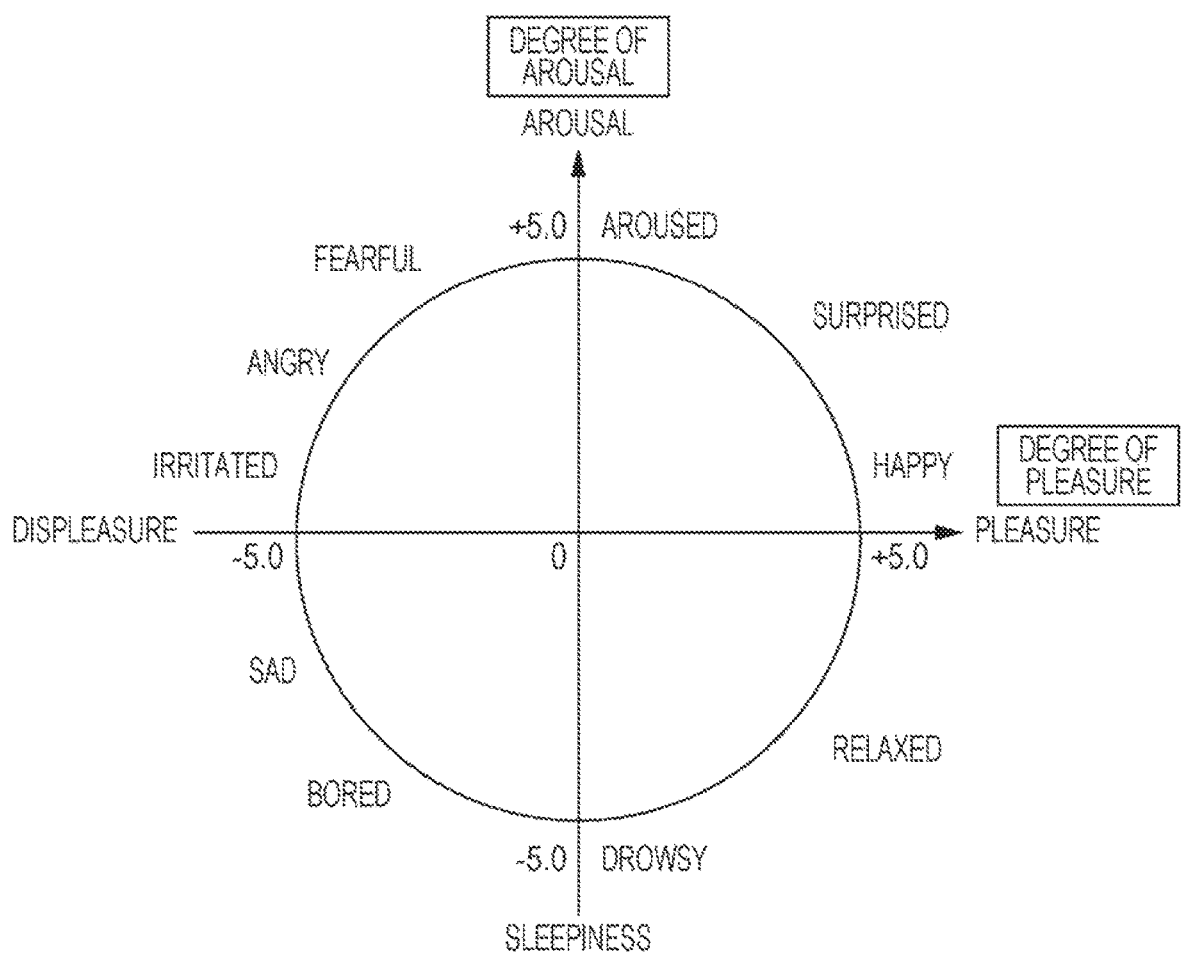
FIG. 2 is a drawing for illustrating an emotional state value calculated by a mood determination unit in the embodiment.

DETAILED DESCRIPTION (Underlying Knowledge Forming Basis of the Present Disclosure)

When a second user contacts a first user with any kind of report matter, the possibility of the second user harming the mood of the first user decreases in a case where contact has been made when the mood of the first user is good compared to when the mood of the first user is bad. However, there is a risk of the report matter of the second user harming the mood of the first user depending on the reason for the mood of the first user being good. For example, in a case where the mood of the first user is good as a result of the first user receiving a good report matter from a person other than the second user, there is a risk of the report matter of the second user being compared with the report matter of the person other than the second user and the report matter of the second user harming the mood of the first user.

In the prior communication terminal device mentioned above, the degree of tension and the degree of calmness of a user are detected on the basis of a pulse rate and an acceleration acquired from a pulse sensor and an acceleration sensor, and the degree of tension and the degree of calmness detected are transmitted to another communication terminal device. However, consideration is not given to the reason for the degree of tension and the degree of calmness of the user having come to be in the current situation.

Furthermore, in the prior communication terminal device mentioned above, although information with which the situation of the user of the transmitting-side communication terminal device can be sufficiently comprehended is transmitted to the user of the receiving-side communication terminal device, information with which the situation of the user of the receiving-side communication terminal device can be sufficiently comprehended is not transmitted to the user of the transmitting-side communication terminal device.

That is, in the aforementioned technology, consideration was not given to the reason leading to the current situation of the transmitting-side user, and further improvement is required.

The present disclosure provides an information processing method, an information processing device, and a recording medium recording an information processing program, which can notify a second user of a timing at which it is possible for a first user to be favorably contacted.

An information processing method according to an aspect of the present disclosure includes: acquiring biological information of a first user holding a first information processing device; detecting a state in which the mood of the first user is estimated as being good on the basis of the biological information; in a case where a state in which the mood of the first user is estimated as being good is detected, estimating a reason for the mood of the first user being good on the basis of behavior history information indicating a behavior history of the first user; and transmitting reason information indicating the estimated reason, to a second information processing device held by a second user who wishes to be notified of a timing for contacting the first user.

According to this configuration, biological information of a first user holding a first information processing device is acquired. A state in which the mood of the first user is estimated as being good on the basis of the biological information is detected. In a case where a state in which the mood of the first user is estimated as being good is detected, a reason for the mood of the first user being good is estimated on the basis of behavior history information indicating a behavior history of the first user. Reason information indicating the estimated reason is transmitted to a second information processing device held by a second user who wishes to be notified of a timing for contacting the first user.

Consequently, because reason information indicating the reason for the mood of the first user being good is transmitted to the second information processing device and, in the second information processing device, a timing for the first user to be contacted is determined on the basis of the reason information and notified to the second user, a timing at which it is possible for the first user to be favorably contacted can be notified to the second user.

Furthermore, in the aforementioned information processing method, in addition, the reason information transmitted by the first information processing device may be received in the second information processing device, in addition, it may be determined whether or not the present point in time is a timing for contacting the first user, on the basis of the received reason information, and, in addition, in a case where it is determined that the present point in time is a timing for contacting the first user, the second user may be notified that the present point in time is a timing for contacting the first user.

According to this configuration, the reason information transmitted by the first information processing device is received in the second information processing device. It is determined whether or not the present point in time is a timing for contacting the first user, on the basis of the received reason information. In a case where it is determined that the present point in time is a timing for contacting the first user, the second user is notified that the present point in time is a timing for contacting the first user.

Consequently, because it can be determined in the second information processing device whether or not the present point in time is a timing for contacting the first user on the basis of the reason information, the processing load of the first information processing device can be reduced.

Furthermore, in the aforementioned information processing method, in the determining, reference may be made to a table having associated therein reasons for the mood of the first user being good and information indicating whether or not it is appropriate to contact the first user, and, in a case where information indicating that it is appropriate to contact the first user is associated with a reason indicated by the received reason information, it may be determined that the present point in time is a timing for contacting the first user.

According to this configuration, in the determining, reference is made to a table having associated therein reasons for the mood of the first user being good and information indicating whether or not it is appropriate to contact the first user, and, in a case where information indicating that it is appropriate to contact the first user is associated with a reason indicated by the received reason information, it is determined that the present point in time is a timing for contacting the first user.

Consequently, in a case where information indicating that it is appropriate to contact the first user is associated with a reason indicated by the received reason information, it is determined that the present point in time is a timing for contacting the first user, and therefore it can be easily determined whether or not the present point in time is a timing for contacting the first user.

Furthermore, in the aforementioned information processing method, in addition, voice information of a dialogue between the first user and a person other than the second user may be acquired, in addition, character strings spoken by the first user may be extracted by performing voice recognition on the voice information, in addition, the extracted character strings may be segmented into items of meaningful speech content, in addition, a speech attribute for classifying according to the speech content may be specified with respect to each segmented character string, and, in addition, in a case where a state in which the mood of the first user is estimated as being good is detected, the behavior history information having associated therein times at which the first user has spoken, the segmented character strings, and the specified speech attributes may be stored in a behavior history storage unit.

According to this configuration, voice information of a dialogue between the first user and a person other than the second user is acquired. Character strings spoken by the first user are extracted by performing voice recognition on the voice information. The extracted character strings are segmented into items of meaningful speech content. A speech attribute for classifying according to the speech content is specified with respect to each segmented character string. In a case where a state in which the mood of the first user is estimated as being good is detected, the behavior history information having associated therein times at which the first user has spoken, the segmented character strings, and the specified speech attributes is stored in a behavior history storage unit.

Consequently, because times at which the first user has spoken, segmented character strings, and specified speech attributes are associated in the behavior history information, a reason for the mood of the first user being good can be estimated according to the speech content of the first user.

Furthermore, in the aforementioned information processing method, in the estimating of the reason, a reason associated with a speech attribute included in the behavior history information may be read from an estimated reason storage unit that associates and stores the speech attributes and reasons for the mood being good estimated from the speech attributes.

According to this configuration, in the estimating of the reason, a reason associated with a speech attribute included in the behavior history information is read from the estimated reason storage unit which associates and stores speech attributes and reasons for the mood being good estimated from the speech attributes.

Consequently, because a reason associated with a speech attribute included in the behavior history information is read from the estimated reason storage unit which associates and stores speech attributes and reasons for the mood being good estimated from the speech attributes, the reason for the mood of the first user being good can be easily estimated.

Furthermore, in the aforementioned information processing method, the estimated reason storage unit may associate and store the speech attributes and a plurality of mutually different reasons, and, in the estimating of the reason, a plurality of mutually different speech attributes of a period in which the mood of the first user has been good may be read from the behavior history storage unit, and the reason that occurs most from among the plurality of reasons respectively associated with the plurality of speech attributes that have been read may be read from the estimated reason storage unit.

According to this configuration, the estimated reason storage unit associates and stores speech attributes and a plurality of mutually different reasons. In the estimating of the reason, a plurality of mutually different speech attributes of a period in which the mood of the first user has been good are read from the behavior history storage unit, and the reason that occurs most from among the plurality of reasons respectively associated with the plurality of speech attributes that have been read is read from the estimated reason storage unit.

Consequently, because the reason that occurs most from among the plurality of reasons respectively associated with the plurality of speech attributes is read from the estimated reason storage unit, the reason for the mood of the first user being good can be accurately estimated from the speech of the first user.

Furthermore, in the aforementioned information processing method, in addition, request information for requesting the reason information transmitted by the second information processing device may be received, and, in the detecting, the request information being received may serve as a trigger for detecting the state in which the mood of the first user is estimated as being good.

According to this configuration, request information for requesting the reason information transmitted by the second information processing device is received. In the detecting, the request information being received serves as a trigger for detection of a state in which the mood of the first user is estimated as being good.

Consequently, because the request information transmitted by the second information processing device being received serves as a trigger for detection of a state in which the mood of the first user is estimated as being good, a timing for contacting the first user can be notified at a timing desired by the second user.

An information communication device according to another aspect of the present disclosure is provided with a processor and a communication unit, in which the processor acquires biological information of a first user holding an information processing device, detects a state in which the mood of the first user is estimated as being good on the basis of the biological information, in a case where the state in which the mood of the first user is estimated as being good is detected, estimates a reason for the mood of the first user being good on the basis of behavior history information indicating a behavior history of the first user, and causes the communication unit to transmit reason information indicating the estimated reason, to another information processing device held by a second user who wishes to be notified of a timing for contacting the first user.

According to this configuration, biological information of a first user holding a first information processing device is acquired. A state in which the mood of the first user is estimated as being good on the basis of the biological information is detected. In a case where a state in which the mood of the first user is estimated as being good is detected, a reason for the mood of the first user being good is estimated on the basis of behavior history information indicating a behavior history of the first user. Reason information indicating the estimated reason is transmitted to a second information processing device held by a second user who wishes to be notified of a timing for contacting the first user.

Consequently, because reason information indicating the reason for the mood of the first user being good is transmitted to the second information processing device and, in the second information processing device, a timing for the first user to be contacted is determined on the basis of the reason information and notified to the second user, a timing at which it is possible for the first user to be favorably contacted can be notified to the second user.

A recording medium according to another aspect of the present disclosure is a non-transitory recording medium recording an information processing program. The information processing program causes a processor provided in a first information processing device to execute processing including: acquiring biological information of a first user holding the first information processing device; detecting a state in which the mood of the first user is estimated as being good on the basis of the biological information; in a case where the state in which the mood of the first user is estimated as being good is detected, estimating a reason for the mood of the first user being good on the basis of behavior history information indicating a behavior history of the first user; and causing a communication unit to transmit reason information indicating the estimated reason, to a second information processing device held by a second user who wishes to be notified of a timing for contacting the first user.

According to this configuration, biological information of a first user holding a first information processing device is acquired. A state in which the mood of the first user is estimated as being good on the basis of the biological information is detected. In a case where a state in which the mood of the first user is estimated as being good is detected, a reason for the mood of the first user being good is estimated on the basis of behavior history information indicating a behavior history of the first user. Reason information indicating the estimated reason is transmitted to a second information processing device held by a second user who wishes to be notified of a timing for contacting the first user.

Consequently, because reason information indicating the reason for the mood of the first user being good is transmitted to the second information processing device and, in the second information processing device, a timing for the first user to be contacted is determined on the basis of the reason information and notified to the second user, a timing at which it is possible for the first user to be favorably contacted can be notified to the second user.

Hereinafter, an embodiment of the present disclosure will be described with reference to the appended drawings. It should be noted that the embodiment hereinafter is an exemplary embodiment of the present disclosure and does not restrict the technical scope of the present disclosure.

Embodiment

FIG. 1 is a block diagram depicting an example of a configuration of an information communication system according to an embodiment of the present disclosure. The information communication system depicted in FIG. 1 is provided with a first information communication device 1 and a second information communication device 2.

The first information communication device 1 and the second information communication device 2 are smartphones, tablet computers, or personal computers, for example. It should be noted that the first information communication device 1 is an example of a first information processing device and an information processing device, and the second information communication device 2 is an example of a second information processing device and another information processing device. The first information communication device 1 is possessed by a first user. The second information communication device 2 is possessed by a second user who wishes to be notified of a timing for contacting the first user.

The first information communication device 1 is communicably connected to the second information communication device 2 via a network 3. It should be noted that the network 3 is the Internet, for example.

The first information communication device 1 is provided with a biological information measurement unit 11, a voice acquisition unit 12, a control unit 13, a storage unit 14, and a communication unit 15.

The biological information measurement unit 11 is constituted by various sensors, for example, and measures biological information of the first user. Furthermore, the biological information measurement unit 11 measures the biological information of the first user at predetermined time intervals. The blood flow, heart rate, pulse rate, brain waves, blood pressure, biogas, respiration, and/or body temperature of the first user are examples of the biological information. For example, the biological information measurement unit 11 is provided with a sensor that measures pulse waves of the first user in a non-contact manner using a highly sensitive spread-spectrum millimeter-wave radar or the like, and detects the heart rate and heartbeat fluctuations of the first user.

It should be noted that the configuration of the biological information measurement unit 11 is not particularly restricted to this example, and a smartwatch that measures biological data or the like of a person may be attached to the first user and biological data or the like may be acquired from the smartwatch. In this case, the first information communication device 1 may be provided with a biological information receiving unit that receives the biological information that has been measured. Furthermore, the biological information measurement unit 11 may be a camera, and may capture the facial expression of the first user and acquire the captured image.

The voice acquisition unit 12 is a microphone, for example, and acquires voice information in the periphery of the first information communication device 1. The voice acquisition unit 12 acquires voice information of a dialogue between the first user and a person other than the second user.

The control unit 13 includes a processor such as a CPU (central processing unit), for example, and controls the entirety of the first information communication device 1. The control unit 13 is provided with a biological information acquisition unit 131, a mood determination unit 132, a behavior history control unit 133, a reason estimation unit 134, and a transmission control unit 135.

The storage unit 14 is a semiconductor memory or a hard disk drive, for example, and is provided with a mood determination history storage unit 141, a behavior history storage unit 142, and a reason estimation database 143.

The biological information acquisition unit 131 acquires biological information of the first user measured by the biological information measurement unit 11.

The mood determination unit 132 detects a state in which the mood of the first user is estimated as being good on the basis of the biological information acquired by the biological information acquisition unit 131. The mood determination unit 132 determines whether or not the mood of the first user is good on the basis of the biological information acquired by the biological information acquisition unit 131. The mood determination unit 132 calculates an emotional state value for the present time on the basis of the biological information. The mood determination unit 132 stores, in advance, a table in which values for biological information and emotional state values are associated, or a function for converting a value for biological information into an emotional state value, for example. The mood determination unit 132 reads an emotional state value associated with the value for the acquired biological information from the table, or substitutes the value for the acquired biological information into the function to calculate an emotional state value.

FIG. 2 is a drawing for illustrating an emotional state value calculated by the mood determination unit in the present embodiment. In FIG. 2, the vertical axis indicates a degree of arousal and the horizontal axis indicates a degree of pleasure.

An emotional state value is represented by two-dimensional coordinates indicating the degree of arousal and the degree of pleasure. The mood determination unit 132 calculates an emotional state value in two-dimensional coordinates. The two-dimensional coordinates depicted in FIG. 2 are based on Russell's circumplex model of affect (James A. Russell, "A Circumplex Model of Affect", Journal of Personality and Social Psychology, 1980, Vol. 39, No. 6, 1161-1178).

The degree of arousal is indicated by a value from −5.0 (sleepiness) to +5.0 (aroused), and the degree of pleasure is indicated by a value from −5.0 (displeasure) to +5.0 (pleasure).

The mood determination unit 132 determines that the mood of the first user is bad in a case where the value for the degree of pleasure of the calculated emotional state value is lower than 0 (−5.0≤degree of pleasure<0 and −5.0≤degree of arousal≤+5.0), and determines that the mood of the first user is good in a case where the value for the degree of pleasure of the calculated emotional state value is equal to or greater than 0 (0≤degree of pleasure≤+5.0 and −5.0≤degree of arousal≤+5.0). In other words, the mood determination unit 132 determines that the mood of the first user is bad in a case where the calculated emotional state value is in the second quadrant or the third quadrant, and determines that the mood of the first user is good in a case where the calculated emotional state value is in the first quadrant or the fourth quadrant.

It should be noted that the mood determination unit 132 may specify the emotion of the first user from the calculated emotional state value, and detect a state in which the mood of the first user is estimated as being good on the basis of the specified emotion of the first user. For example, the mood determination unit 132 may determine that the mood of the first user is bad in a case where the emotion of the first user specified from the calculated emotional state value is "angry", and determine that the mood of the first user is good in a case where the emotion of the first user specified from the calculated emotional state value is an emotion other than "angry". Furthermore, the mood determination unit 132 may determine that the mood of the first user is good in a case where the emotion of the first user specified from the calculated emotional state value is "happy".

Furthermore, the determination of the mood of the first user by the mood determination unit 132 is not restricted to the aforementioned, and a state in which the mood of the first user is estimated as being good may be detected using at least one of the facial expression of the first user, the leg movements of the first user, and the speech volume of the first user. Japanese Unexamined Patent Application Publication No. 2012-146208 discloses determining the mood of a first user using at least one of the facial expression of the first user, the leg movements of the first user, and the speech volume of the first user.

Furthermore, the mood determination unit 132 may input a plurality of items of biological information of the first user into a recognition algorithm that is based on a machine learning method and recognize the emotion of the first user.

In addition, with regard to the method for determining whether or not the mood of the first user is good, it is possible to use the techniques disclosed in International Publication No. 2016/170810, Japanese Unexamined Patent Application Publication No. 2009-208727, and Japanese Unexamined Patent Application Publication No. 2015-46065, for example.

The mood determination history storage unit 141 associates and stores a time determined by the mood determination unit 132 and a value for the degree of pleasure of the emotional state value calculated by the mood determination unit 132.

FIG. 3 is a drawing depicting an example of the mood determination history stored in the mood determination history storage unit in the present embodiment. In FIG. 3, biological information is acquired every 15 seconds, for example, and whether or not the mood of the first user is good is determined every 15 seconds, for example. In FIG. 3, a degree of pleasure of "2.5" is associated with the time "10:00:00", a degree of pleasure of "3.0" is associated with the time "10:00:15", and a degree of pleasure of "3.5" is associated with the time "10:00:30", for example. It should be noted that the mood determination history storage unit 141 stores determination times and degrees of pleasure with respect to a user ID for identifying the first user.

It should be noted that the timing for acquiring the biological information and the timing for determining the mood of the first user are not restricted to the aforementioned every 15 seconds.

The mood determination unit 132 stores a mood determination history having associated therein the time at which a determination was performed and the value for the degree of pleasure of the calculated emotional state value, in the mood determination history storage unit 141. It should be noted that the mood determination unit 132 may store a mood determination history having associated therein the time at which a determination was performed and information indicating whether or not the mood of the first user is good, in the mood determination history storage unit 141. Furthermore, the mood determination unit 132 may store a mood determination history having associated therein the time at which a determination was performed and information indicating that the mood of the first user is good, in the mood determination history storage unit 141.

The behavior history control unit 133 stores behavior history information indicating a history of the behavior of the first user in the behavior history storage unit 142.

Figure 4:
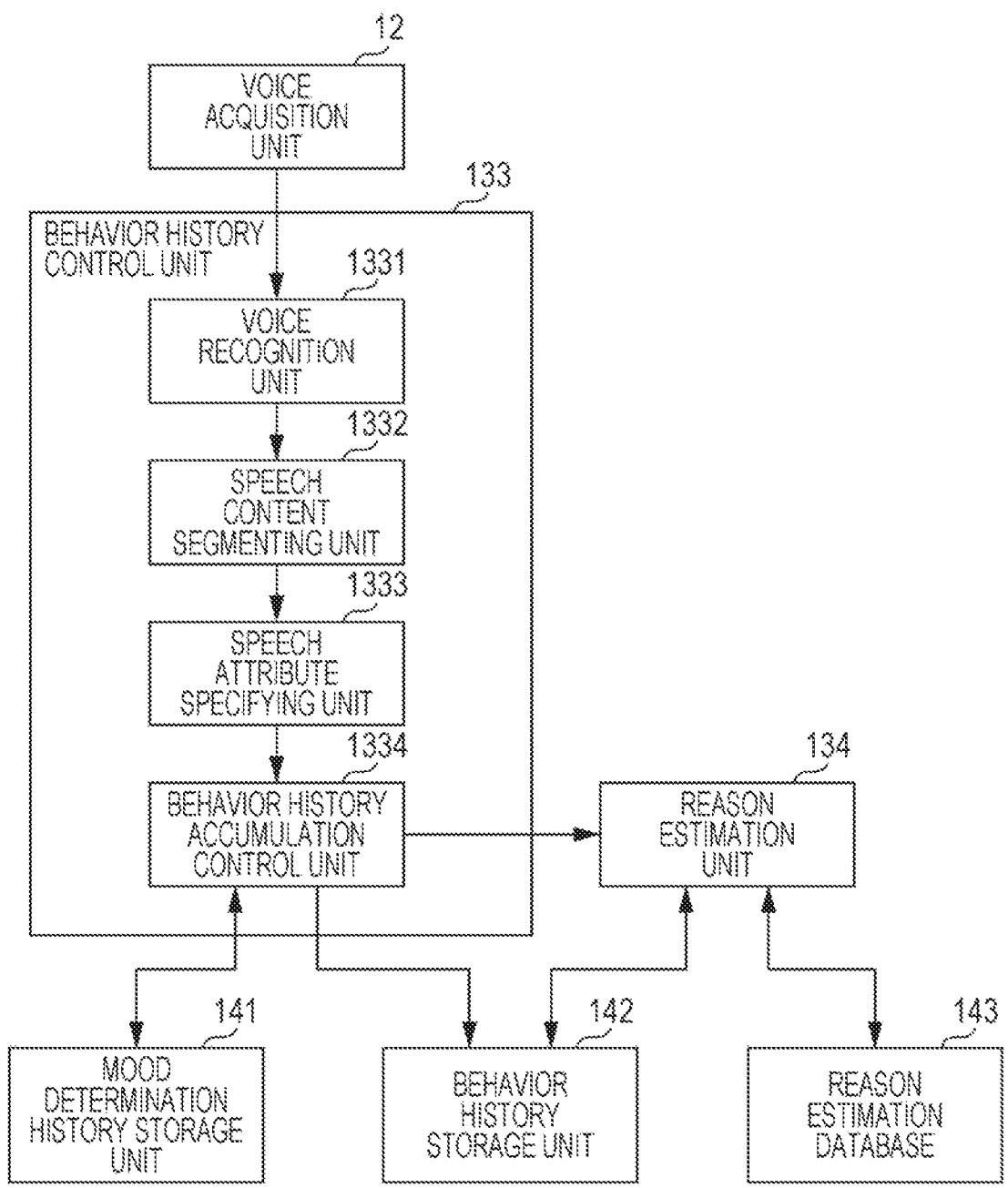
FIG. 4 is a block diagram depicting a configuration of a behavior history control unit depicted in FIG. 1.

FIG. 4 is a block diagram depicting a configuration of the behavior history control unit depicted in FIG. 1. The behavior history control unit 133 depicted in FIG. 4 is provided with a voice recognition unit 1331, a speech content segmenting unit 1332, a speech attribute specifying unit 1333, and a behavior history accumulation control unit 1334.

The voice recognition unit 1331 extracts character strings spoken by the first user, by performing voice recognition on the voice information acquired by the voice acquisition unit 12.

The speech content segmenting unit 1332 segments the character strings extracted by the voice recognition unit 1331, into items of meaningful speech content.

The speech attribute specifying unit 1333 specifies speech attributes for classifying according to speech content, with respect to each character string segmented by the speech content segmenting unit 1332, on the basis of a speech attribute database (not depicted) having associated therein character strings and speech attributes for classifying according to speech content. It should be noted that the storage unit 14 may be provided with the speech attribute database. For example, the speech attribute of "compliment" is associated with the character string of "you did well", and the speech attribute of "encouragement" is associated with the character string of "keep up the good work", Furthermore, character strings such as "well done" and "excellent" are associated with the speech attribute of "compliment", and character strings such as "keep it up" and "carry on like this" are associated with the speech attribute of "encouragement". It should be noted that the speech attribute specifying unit 1333 may discard a segmented character string in a case where a speech attribute corresponding to the character string is not present in the speech attribute database.

In a case where a state in which the mood of the first user is estimated as being good is detected, the behavior history accumulation control unit 1334 accumulates, in the behavior history storage unit 142, behavior history information having associated therein times at which the first user has spoken, segmented character strings, and specified speech attributes.

The behavior history storage unit 142 stores behavior history information having associated therein segmented character strings and speech attributes for classifying according to speech content.

FIG. 5 is a drawing depicting an example of behavior history information accumulated by the behavior history accumulation control unit in the present embodiment.

As depicted in FIG. 5, the behavior history information is information having associated therein the times at which the first user has spoken, information specifying the speaker, the degree of pleasure of the speaker at the point in time of speaking, spoken character strings, and speech attributes. The information specifying the speaker may be a user ID for identifying the first user. The degree of pleasure is acquired from the mood determination history storage unit 141. In other words, the behavior history accumulation control unit 1334 reads a degree of pleasure corresponding to the same time as the time of speaking from the mood determination history storage unit 141. It should be noted that, in a case where a degree of pleasure corresponding to the same time as the time of speaking is not present in the mood determination history storage unit 141, the behavior history accumulation control unit 1334 may read a degree of pleasure corresponding to the time immediately preceding the time of speaking or the time immediately subsequent to the time of speaking. For example, in a case where a degree of pleasure corresponding to the time "12:50:13" is not present in the mood determination history storage unit 141, the behavior history accumulation control unit 1334 may read the degree of pleasure corresponding to the time "12:50:15", A spoken character string is a character string that has been segmented by the speech content segmenting unit 1332.

It should be noted that the behavior history accumulation control unit 1334 may read a degree of pleasure of a predetermined time prior to the time of speaking from the mood determination history storage unit 141. Furthermore, it should be noted that the behavior history accumulation control unit 1334 may read a degree of pleasure of a predetermined time subsequent to the time of speaking from the mood determination history storage unit 141. In addition, the behavior history accumulation control unit 1334 may read a plurality of degrees of pleasure from within a predetermined time period based on the time of speaking from the mood determination history storage unit 141, and the average of the plurality of degrees of pleasure that have been read may serve as a degree of pleasure of the behavior history information. It should be noted that the predetermined time period indicates a period between the time of speaking and the time at a predetermined time prior to the time of speaking, for example.

The behavior history accumulation control unit 1334 stores behavior history information having associated therein the time "12:50:00", information specifying the first user who is the speaker, the degree of pleasure "3.0", the spoken character string "you did well", and the speech attribute "compliment", for example.

It should be noted that, in the present embodiment, the behavior history accumulation control unit 1334 accumulates behavior history information in which the degree of pleasure is equal to or greater than 3.0 in the behavior history storage unit 142. The behavior history accumulation control unit 1334 may accumulate behavior history information generated in a case where it is determined that the mood is good, in other words, in a case where the degree of pleasure is equal to or greater than 0, in the behavior history storage unit 142. The amount of information stored in the behavior history storage unit 142 can be reduced by accumulating behavior history information having a degree of pleasure that is equal to or greater than a predetermined value in the behavior history storage unit 142.

In a case where a state in which the mood of the first user is estimated as being good has been detected by the mood determination unit 132, the reason estimation unit 134 estimates the reason for the mood of the first user being good on the basis of behavior history information indicating the behavior history of the first user. In a case where a state in which the mood of the first user is estimated as being good has been detected by the mood determination unit 132, the reason estimation unit 134 acquires behavior history information indicating the behavior history of the first user from the behavior history storage unit 142.

The reason estimation database 143 associates and stores speech attributes and reasons for the mood being good estimated from the speech attributes.

FIG. 6 is a drawing depicting an example of reason information stored in the reason estimation database in the present embodiment. For example, reasons for the mood of the first user being good such as "praise" and "praise highly" are associated with the speech attribute of "compliment", and reasons for the mood of the first user being good such as "encourage" and "praise" are associated with the speech attribute of "encouragement".

The reason estimation unit 134 reads a reason associated with a speech attribute included in the behavior history information from the reason estimation database 143. The reason estimation unit 134 can thereby estimate the reason for the mood of the first user being good.

It should be noted that at least one reason may be associated with one speech attribute, and the reason estimation database 143 may associate and store an attribute and a plurality of mutually different reasons. In this case, the reason estimation unit 134 may extract a plurality of mutually different speech attributes of a period in which the mood of the first user has been good, from the behavior history information, and read the reason that occurs the most from among a plurality of reasons respectively associated with the plurality of extracted speech attributes, from the reason estimation database. For example, the reason estimation unit 134 extracts speech attributes having a degree of pleasure that is equal to or greater than 3.0 from within a period from the point in time at which it was determined that the mood of the first user is good to a predetermined time prior thereto, from the behavior history storage unit 142. In FIG. 6, in a case where the two speech attributes of "compliment" and "encouragement" have been extracted from the behavior history storage unit 142, the reason of "praise" appears twice for "compliment" and "encouragement", and therefore the reason estimation unit 134 reads "praise" from the reason estimation database 143 as the reason for the mood of the first user being good.

It should be noted that the reason estimation unit 134 may randomly read one reason from among the plurality of reasons respectively associated with the plurality of extracted speech attributes. Furthermore, priority rankings may be given to the reasons, and the reason estimation unit 134 may read the reason having the highest priority ranking from among the plurality of reasons respectively associated with the plurality of extracted speech attributes.

The transmission control unit 135 transmits reason information indicating the reason estimated by the reason estimation unit 134 to the second information communication device 2, which is held by the second user who wishes to be notified of a timing for contacting the first user and which determines and notifies the timing on the basis of the reason information.

The communication unit 15 transmits information to the second information communication device 2 and also receives information from the second information communication device 2. The communication unit 15 may include a communication circuit, for example, and the aforementioned transmitting of information and receiving of information may be performed by the communication circuit. The communication unit 15 transmits the reason information to the second information communication device 2 in accordance with control performed by the transmission control unit 135.

The second information communication device 2 is provided with a communication unit 21, a control unit 22, a storage unit 23, a notification unit 24, and an input unit 25.

The communication unit 21 receives information from the first information communication device 1 and also transmits information to the first information communication device 1. The communication unit 21 may include a communication circuit, for example, and the aforementioned transmitting of information and receiving of information may be performed by the communication circuit. The communication unit 21 receives the reason information transmitted by the first information communication device 1.

The control unit 22 is a CPU, for example, and controls the entirety of the second information communication device 2. The control unit 22 is provided with a timing determination unit 221.

The storage unit 23 is a semiconductor memory or a hard disk drive, for example, and is provided with a timing storage unit 231.

The timing storage unit 231 associates and stores reason information indicating the reason for the mood of the first user being good, and contact advisability information indicating whether or not it is appropriate for the second user to contact the first user.

FIG. 7 is a drawing depicting an example of the contact advisability information stored in the timing storage unit in the present embodiment. In FIG. 7, for example, contact advisability information indicating that it is not a timing at which the second user can contact the first user is associated with the reason of "praise", contact advisability information indicating that it is a timing at which the second user can contact the first user is associated with the reason of "encourage", and contact advisability information indicating that it is a timing at which the second user can contact the first user is associated with the reason of "reprimand".

The timing determination unit 221 determines whether or not the present point in time is a timing for the second user to contact the first user on the basis of the reason information received by the communication unit 21. The timing determination unit 221 refers to the timing storage unit 231 having associated therein reasons for the mood of the first user being good and information indicating whether or not it is appropriate to contact the first user, and determines that the present point in time is a timing for contacting the first user in a case where information indicating that it is appropriate to contact the first user is associated with the reason indicated by the received reason information.

In other words, the timing determination unit 221 refers to the timing storage unit 231, and determines that the present point in time is not a timing at which the second user can contact the first user in a case where the contact advisability information associated with the reason information received by the communication unit 21 is contact advisability information indicating that it is not a timing at which the second user can contact the first user. Furthermore, the timing determination unit 221 refers to the timing storage unit 231, and determines that the present point in time is a timing at which the second user can contact the first user in a case where the contact advisability information associated with the reason information received by the communication unit 21 is contact advisability information indicating that it is a timing at which the second user can contact the first user.

For example, in a case where the reason information received by the communication unit 21 is "praise", contact advisability information indicating that it is not a timing at which the second user can contact the first user is associated with this reason information, and therefore the timing determination unit 221 determines that the present point in time is not a timing at which the second user can contact the first user. However, in a case where the reason information received by the communication unit 21 is "encourage", contact advisability information indicating that it is a timing at which the second user can contact the first user is associated with this reason information, and therefore the timing determination unit 221 determines that the present point in time is a timing at which the second user can contact the first user.

The notification unit 24 is a liquid crystal display device or a touch panel display and, in a case where the timing determination unit 221 has determined that the present point in time is a timing at which the second user can contact the first user, notifies the second user that the present point in time is a timing at which the first user can be contacted. The notification unit 24 displays, on a screen, an image for notifying the second user that the present point in time is a timing at which the first user can be contacted.

It should be noted that the notification unit 24 may be a speaker, for example. In this case, the notification unit 24 outputs a voice or a warning sound for notifying the second user that the present point in time is a timing at which the first user can be contacted. The notification unit 24 may be a light-emitting diode, for example. In this case, the notification unit 24 turns on in a case where it is determined that the present point in time is a timing at which the first user can be contacted, and turns off in a case where it is determined that the present point in time is not a timing at which the first user can be contacted.

It should be noted that the notification unit 24 may mutually vary the color of light emitted in a case where it is determined that the present point in time is a timing at which the first user can be contacted, and the color of light emitted in a case where it is determined that the present point in time is not a timing at which the first user can be contacted. For example, the notification unit 24 may emit blue light in a case where it is determined that the present point in time is a timing at which the first user can be contacted, and emit red light in a case where it is determined that the present point in time is not a timing at which the first user can be contacted.

Furthermore, the notification unit 24 may mutually vary the light emission pattern for a case where it is determined that the present point in time is a timing at which the first user can be contacted, and the light emission pattern for a case where it is determined that the present point in time is not a timing at which the first user can be contacted. For example, the notification unit 24 may cause a light to be continuously lit in a case where it is determined that the present point in time is a timing at which the first user can be contacted, and cause the light to flash in a case where it is determined that the present point in time is not a timing at which the first user can be contacted.

The input unit 25 is a touch panel display, a keyboard, or a mouse, for example, and receives various input operations performed by the second user. The input unit 25 receives an input operation for requesting notification of a timing for contacting the first user. When an input operation for requesting notification of a timing for contacting the first user is received by the input unit 25, the communication unit 21 transmits request information for requesting reason information to the first information communication device 1. The communication unit 15 of the first information communication device 1 receives the request information for requesting reason information transmitted by the second information communication device 2. The request information being received serves as a trigger for the mood determination unit 132 to then detect a state in which the mood of the first user is estimated as being good.

Figure 8:
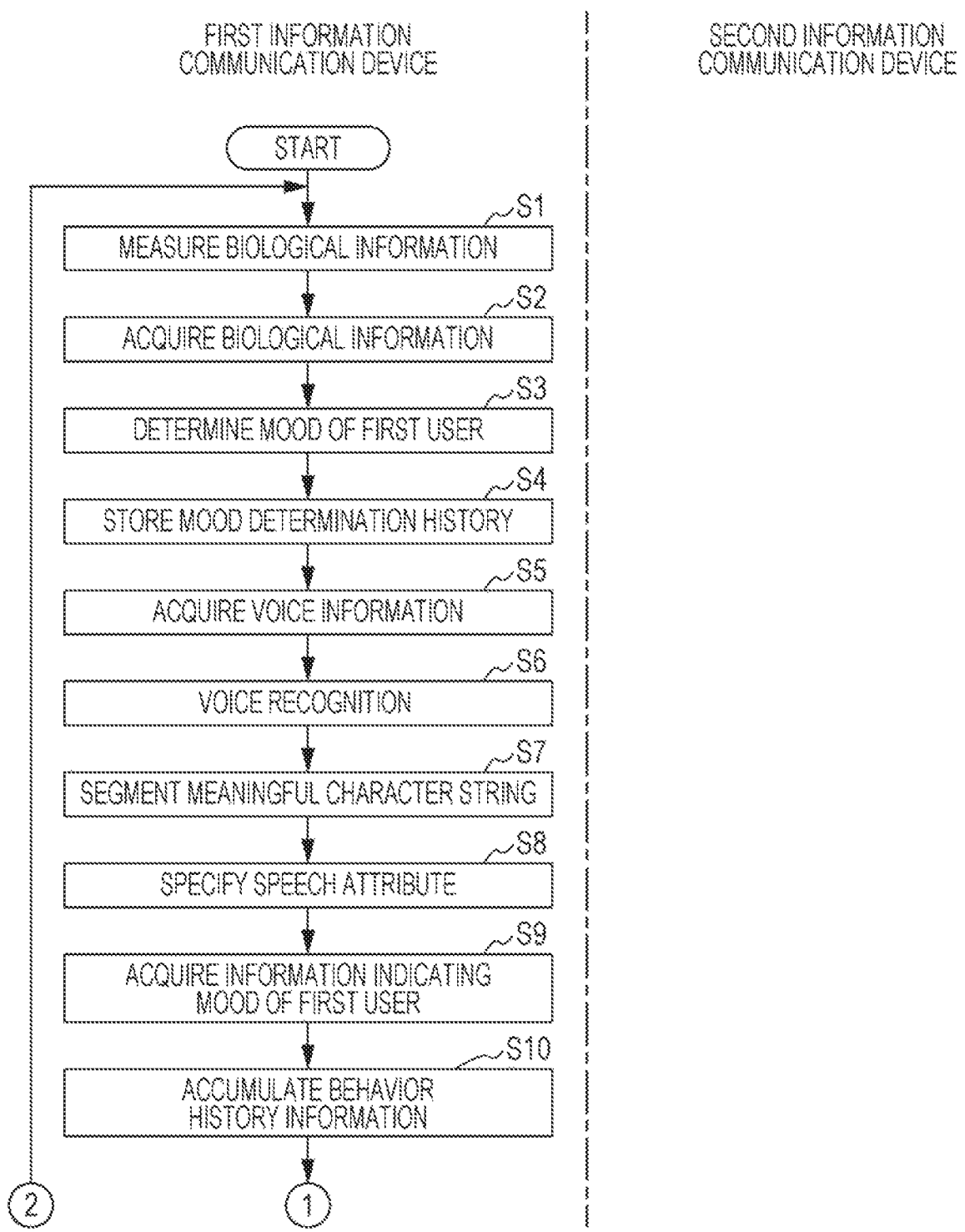
FIG. 8 is a first flowchart for illustrating an operation of the information communication system in the embodiment.
Figure 9:
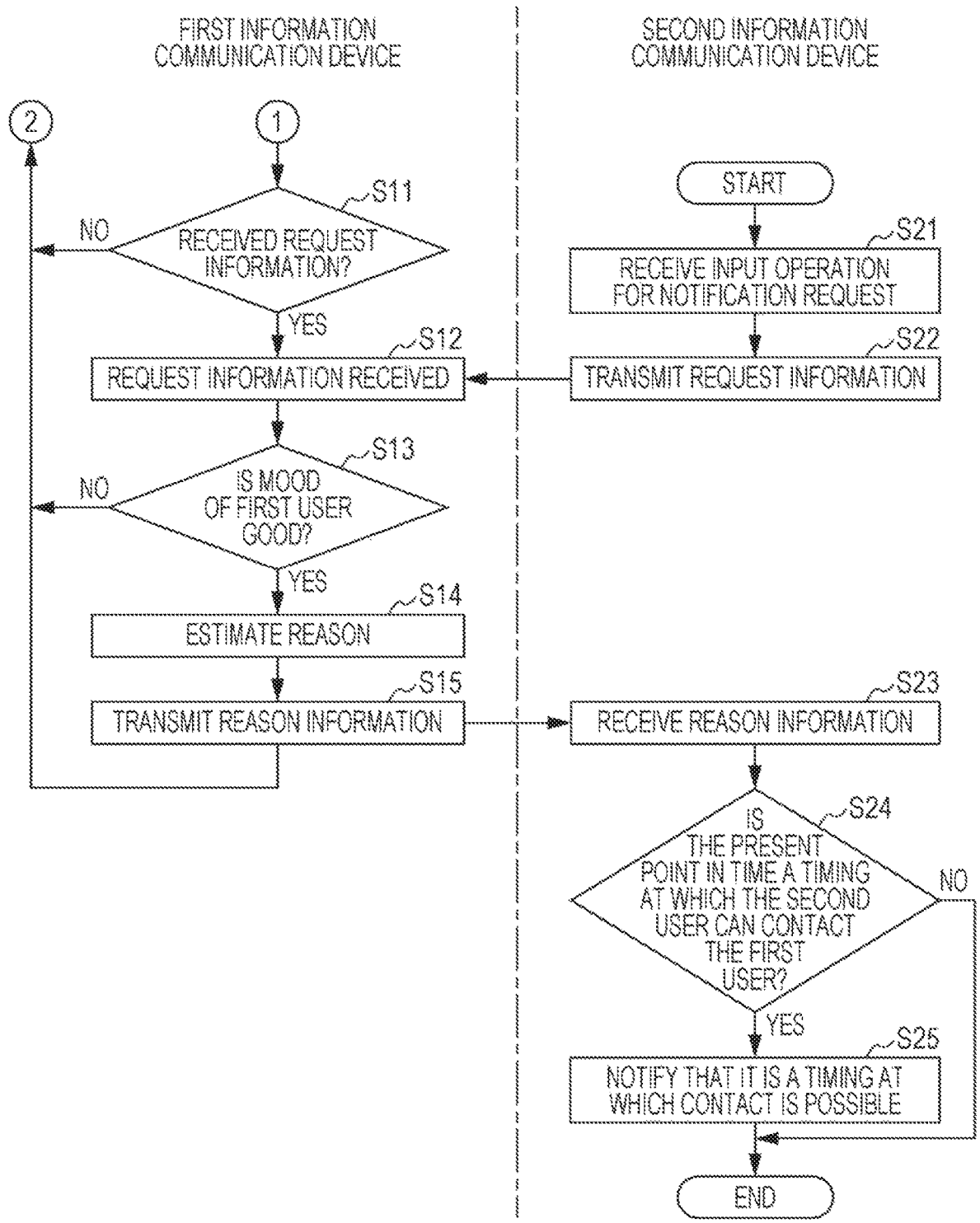
FIG. 9 is a second flowchart for illustrating an operation of the information communication system in the embodiment.

FIG. 8 is a first flowchart for illustrating an operation of the information communication system in the present embodiment, and FIG. 9 is a second flowchart for illustrating an operation of the information communication system in the present embodiment.

First, in step S1, the biological information measurement unit 11 of the first information communication device 1 measures biological information of the first user.

Next, in step S2, the biological information acquisition unit 131 acquires the biological information of the first user measured by the biological information measurement unit 11.

Next, in step S3, the mood determination unit 132 determines whether or not the mood of the first user is good on the basis of the biological information acquired by the biological information acquisition unit 131.

Next, in step S4, the mood determination unit 132 stores a mood determination history having associated therein the time at which it was determined whether or not the mood of the first user is good, and whether or not the mood of the first user is good, in the mood determination history storage unit 141. Here, the time at which it was determined whether or not the mood of the first user is good, and a value for the degree of pleasure of an emotional state value calculated at the time of the determination, are associated in the mood determination history.

Next, in step S5, the voice acquisition unit 12 acquires voice information of a dialogue between the first user and a person other than the second user.

Next, in step S6, the voice recognition unit 1331 extracts character strings spoken by the first user, by performing voice recognition on the voice information acquired by the voice acquisition unit 12.

Next, in step S7, the speech content segmenting unit 1332 segments the character strings extracted by the voice recognition unit 1331, into items of meaningful speech content.

Next, in step S8, the speech attribute specifying unit 1333 specifies speech attributes corresponding to the character strings segmented by the speech content segmenting unit 1332, from a speech attribute database. The speech attribute database associates and stores, in advance, speech attributes for classifying according to speech content, and character strings.

Next, in step S9, the behavior history accumulation control unit 1334 acquires information indicating the mood of the first user corresponding to the time at which the voice information was acquired, from the mood determination history storage unit 141. In a case where values for degrees of pleasure of emotional state values are stored in the mood determination history storage unit 141, the behavior history accumulation control unit 1334 acquires the value for the degree of pleasure corresponding to the time at which the voice information was acquired, from the mood determination history storage unit 141.

Next, in step S10, the behavior history accumulation control unit 1334 accumulates behavior history information having associated therein the times at which the first user has spoken, information specifying the speaker, information indicating the mood of the speaker at the point in time of speaking, spoken character strings, and speech attributes, in the behavior history storage unit 142.

Next, in step S11, the mood determination unit 132 determines whether or not request information for requesting reason information transmitted by the second information communication device 2 has been received. Here, in a case where it is determined that the request information has not been received ("no" in step S11), processing returns to step S1.

In step S21, the input unit 25 of the second information communication device 2 receives an input operation for requesting notification of a timing for contacting the first user.

Next, in step S22, when an input operation for a notification request is received by the input unit 25, the communication unit 21 transmits request information for requesting reason information to the first information communication device 1.

In a case where it is determined that request information has been received ("yes" in step S11), in step S12, the communication unit 15 receives the request information transmitted by the second information communication device 2.

Next, in step S13, the mood determination unit 132 determines whether or not the mood of the first user is good on the basis of the biological information acquired by the biological information acquisition unit 131. Here, in a case where it is determined that the mood of the first user is not good ("no" in step S13), processing returns to step S1.

However, in a case where it is determined that the mood of the first user is good ("yes" in step S13), in step 314, the reason estimation unit 134 estimates the reason for the mood of the first user being good on the basis of behavior history information indicating the behavior history of the first user. At such time, the reason estimation unit 134 acquires a speech attribute from within a predetermined time from the present time from the behavior history storage unit 142, and reads a reason associated with the acquired speech attribute from the reason estimation database 143. The reason estimation unit 134 thereby estimates the reason for the mood of the first user being good.

Next, in step S15, the transmission control unit 135 transmits reason information indicating the reason estimated by the reason estimation unit 134 to the second information communication device 2. It should be noted that, after the processing of step S15, the first information communication device 1 returns to the processing of step S1.

Nest, in step S23, the communication unit 21 of the second information communication device 2 receives the reason information transmitted by the first information communication device 1.

Next, in step S24, the timing determination unit 221 determines whether or not the present point in time is a timing at which the second user can contact the first user on the basis of the reason information received by the communication unit 21. For example, in a case where the reason information received by the communication unit 21 is "praise", the timing determination unit 221 determines that the present point in time is not a timing at which the second user can contact the first user. Furthermore, for example, in a case where the reason information received by the communication unit 21 is a reason other than "praise", the timing determination unit 221 determines that the present point in time is a timing at which the second user can contact the first user. It should be noted that, even if the reason information received by the communication unit 21 is a reason other than "praise", there are cases where the timing determination unit 221 determines that the present point in time is not a timing at which the second user can contact the first user.

Here, in a case where it is determined that the present point in time is not a timing at which the second user can contact the first user ("no" in step S24), processing ends.

However, in a case where it is determined that the present point in time is a timing at which the second user can contact the first user ("yes" in step S24), in step S25, the notification unit 24 notifies the second user that the present point in time is a timing at which the first user can be contacted. For example, the notification unit 24 displays, on a screen, an image for notifying the second user that the present point in time is a timing at which the first user can be contacted. It should be noted that the second user attempts to contact the first user when notified that the present point in time is a timing at which the first user can be contacted. At such time, the second user orally conveys some kind of report matter to the first user. It should be noted that the second user may convey some kind of report matter to the first user by email.

For example, in a case where the first user is a superior of the second user and the second user is a subordinate of the first user, the second user may wish to convey the report matter when the mood of the first user is good. However, if the second user conveys a report matter to the first user in a case where the mood of the first user is good as a result of praising another person, for example, there is a risk of the report matter of the second user being compared with the report matter of the other person, and there is a risk of the report matter of the second user harming the mood of the first user.

However, in the present embodiment, rather than it being simply determined and notified whether or not the mood of the first user is good, the reason for the mood of the first user being good is estimated and the second user is notified that the present point in time is a timing at which the first user can be contacted on the basis of the estimated reason. Consequently, a timing at which it is possible for the first user to be favorably contacted can be notified to the second user.

In the present embodiment, the control unit 22 of the second information communication device 2 is provided with the timing determination unit 221, and the storage unit 23 of the second information communication device 2 is provided with the timing storage unit 231; however, it should be noted that the present disclosure is not particularly restricted thereto, and the control unit 13 of the first information communication device 1 may be provided with a timing determination unit, and the storage unit 14 of the first information communication device 1 may be provided with a timing storage unit.

In this case, the timing determination unit determines whether or not the present point in time is a timing for the second user to contact the first user on the basis of a reason estimated by the reason estimation unit 134. In a case where it is determined that the present point in time is a timing for contacting the first user, the communication unit 15 transmits notification information notifying that the present point in time is a timing for contacting the first user to the second information communication device 2. The communication unit 21 of the second information communication device 2 receives the notification information transmitted by the first information communication device 1. When the notification information has been received by the communication unit 21, the notification unit 24 then notifies the second user that the present point in time is a timing for contacting the first user.

Furthermore, in the present embodiment, the voice acquisition unit 12 acquires voice information of a dialogue between the first user and a person other than the second user; however, the present disclosure is not particularly restricted thereto, and the voice acquisition unit 12 may acquire voice information of a dialogue between the first user and the second user. In this case, the communication unit 15 may transmit reason information to a third information communication device possessed by a third user who wishes to be notified of a timing for contacting the first user.

Hereinabove, the device of the present disclosure has been described on the basis of an embodiment; however, the present disclosure is not restricted to this embodiment. Modes in which various modifications conceived by a person skilled in the art have been implemented in the present embodiment, and modes constructed by combining the constituent elements in different embodiments may also be included within the scope of the one or more aspects of the present disclosure provided they do not depart from the gist of the present disclosure.

It should be noted that, in the aforementioned embodiment; the constituent elements may be configured by using dedicated hardware, or may be realized by executing a software program suitable for the constituent elements. The constituent elements may be realized by a program execution unit such as a CPU or a processor reading out and executing a software program recorded in a recording medium such as a hard disk or a semiconductor memory.

Some or all of the functions of the device according to the embodiment of the present disclosure are typically realized as an LSI (large scale integration), which is an integrated circuit. These may be implemented separately as single chips; or may be implemented as a single chip in such a way as to include some or all of the functions. Furthermore, the circuit integration is not restricted to an LSI, and the functions may be realized using a dedicated circuit or a general-purpose processor. After an LSI is manufactured, a field-programmable gate array (FPGA) that can be programmed, or a reconfigurable processor with which the connections and settings of circuit cells within the LSI can be reconfigured, may be used.

Furthermore, some or all of the functions of the device according to the embodiment of the present disclosure may be realized by a processor such as a CPU executing a program.

Furthermore, the numerals used hereinabove are all examples for explaining the present disclosure in a specific manner, and the present disclosure is not limited to the numerals given as examples.

Furthermore, the order in which the steps depicted in the aforementioned flowcharts is executed is an exemplary order for describing the present disclosure in a specific manner, and may be an order other than the aforementioned provided a similar effect can be obtained. Furthermore, some of the steps may be executed at the same time as (in parallel with) other steps.

In addition, various modified examples obtained by implementing alterations that are within the scope and conceived by a person skilled in the art with respect to the embodiment of the present disclosure are also included in the present disclosure provided they do not depart from the gist of the present disclosure.

An information processing method, an information processing device, and a recording medium recording an information processing program according to the present disclosure can notify a second user of a timing at which it is possible for a first user to be favorably contacted, and are useful as an information processing method, an information processing device, and a recording medium recording an information processing program that transmit information to another information processing device.

What is claimed is:

1. An information processing method including:
    acquiring biological information of a first user holding a first information processing device;
    detecting a state in which a mood of the first user is estimated as being good on the basis of the biological information;
    in a case where the state in which the mood of the first user is estimated as being good is detected, estimating a reason for the mood of the first user being good on the basis of behavior history information indicating a behavior history of the first user; and
    transmitting reason information indicating the estimated reason, to a second information processing device held by a second user who wishes to be notified of a timing for contacting the first user.

2. The information processing method according to claim 1, wherein,
    in addition, the reason information transmitted by the first information processing device is received in the second information processing device,
    in addition, it is determined whether or not a present point in time is a timing for contacting the first user, on the basis of the received reason information, and,
    in addition, in a case where it is determined that the present point in time is a timing for contacting the first user, the second user is notified that the present point in time is a timing for contacting the first user.

3. The information processing method according to claim 2, wherein,
    in the determining, reference is made to a table having associated therein reasons for the mood of the first user being good and information indicating whether or not it is appropriate to contact the first user, and,
    in a case where information indicating that it is appropriate to contact the first user is associated with a reason indicated by the received reason information, it is determined that the present point in time is a timing for contacting the first user.

4. The information processing method according to claim 1, wherein,
    in addition, voice information of a dialogue between the first user and a person other than the second user is acquired,
    in addition, character strings spoken by the first user are extracted by performing voice recognition on the voice information,
    in addition, the extracted character strings are segmented into items of meaningful speech content,
    in addition, a speech attribute for classifying according to the speech content is specified with respect to each segmented character string, and,
    in addition, in a case where the state in which the mood of the first user is estimated as being good is detected, the behavior history information having associated therein times at which the first user has spoken, the segmented character strings, and the specified speech attributes is stored in a behavior history storage.

5. The information processing method according to claim 4, wherein,
    in the estimating of the reason, a reason associated with a speech attribute included in the behavior history information is read from an estimated reason storage that associates and stores the speech attributes and reasons for the mood being good estimated from the speech attributes.

6. The information processing method according to claim 5, wherein,
    the estimated reason storage associates and stores the speech attributes and a plurality of mutually different reasons, and,
    in the estimating of the reason, a plurality of mutually different speech attributes of a period in which the mood of the first user has been good are read from the behavior history storage, and a reason that occurs most from among the plurality of reasons respectively associated with the plurality of speech attributes that have been read is read from the estimated reason storage.

7. The information processing method according to claim 1, wherein,
    in addition, request information for requesting the reason information transmitted by the second information processing device is received, and,
    in the detecting, the request information being received serves as a trigger for detecting the state in which the mood of the first user is estimated as being good.

8. An information communication device comprising:
    a processor; and
    a communicator,
    wherein the processor
    acquires biological information of a first user holding an information processing device,
    detects a state in which a mood of the first user is estimated as being good on the basis of the biological information,
    in a case where the state in which the mood of the first user is estimated as being good is detected, estimates a reason for the mood of the first user being good on the basis of behavior history information indicating a behavior history of the first user, and
    causes the communicator to transmit reason information indicating the estimated reason, to another information processing device held by a second user who wishes to be notified of a timing for contacting the first user.

9. A non-transitory recording medium recording an information processing program,
    the information processing program causing a processor provided in a first information processing device to execute processing including:
    acquiring biological information of a first user holding a first information processing device;
    detecting a state in which a mood of the first user is estimated as being good on the basis of the biological information;
    in a case where the state in which the mood of the first user is estimated as being good is detected, estimating a reason for the mood of the first user being good on the basis of behavior history information indicating a behavior history of the first user; and
    causing a communicator to transmit reason information indicating the estimated reason, to a second information processing device held by a second user who wishes to be notified of a timing for contacting the first user.

* * * * *